United States Patent [19]
Grover

[11] Patent Number: 4,857,548
[45] Date of Patent: Aug. 15, 1989

[54] METHOD OF PREVENTING OR REDUCING PLATELET LOSS DURING EXTRACORPOREAL CIRCULATION USING A THROMBOXANE $A_2$ RECEPTOR ANTAGONIST

[75] Inventor: Gary J. Grover, Stockton, N.J.

[73] Assignee: E. R. Squibb & Sons, Inc., Princeton, N.J.

[21] Appl. No.: 272,357

[22] Filed: Nov. 17, 1988

Related U.S. Application Data

[62] Division of Ser. No. 165,065, Mar. 7, 1988.

[51] Int. Cl.$^4$ .............................................. A61K 31/34
[52] U.S. Cl. ................................................... 514/469
[58] Field of Search ........................................ 514/467

Primary Examiner—Stanley J. Friedman
Attorney, Agent, or Firm—B. Rodney

[57] ABSTRACT

A method is provided for preventing or reducing platelet loss during extracorporeal circulation, such as during coronary artery bypass of graft surgery by administering a thromboxane $A_2$ antagonist alone or with prostacyclin and/or a prostacyclin mimic.

20 Claims, 1 Drawing Sheet

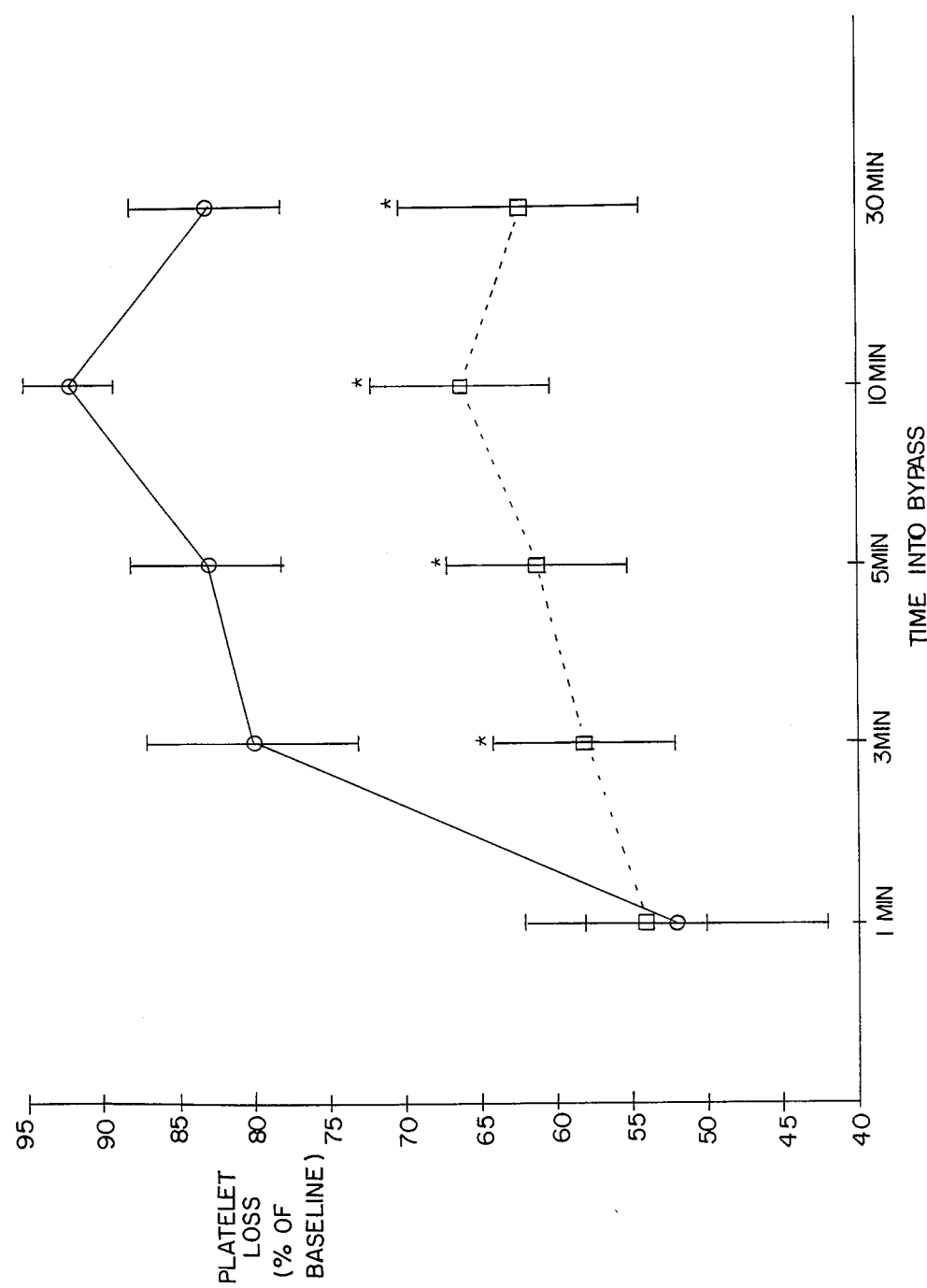

METHOD OF PREVENTING OR REDUCING PLATELET LOSS DURING EXTRACORPOREAL CIRCULATION USING A THROMBOXANE A₂ RECEPTOR ANTAGONIST

This is a division of application Ser. No. 165,065, filed Mar. 7, 1988.

FIELD OF THE INVENTION

The present invention relates to a method for preventing or reducing platelet loss during extracorporeal circulation, for example, during coronary artery bypass and graft procedures or dialysis, by administering a thromboxane A₂ receptor antagonist prior to surgery.

BACKGROUND OF THE INVENTION

Coronary artery bypass and graft (CABG) is a common procedure for restoring blood flow to cardiac regions made ischemic due to blockage of the coronary arteries via atherosclerotic lesions. While the CABG procedure is commonly performed, there are still problems associated with it. One problem is that in order to perform the bypass, the surgeon requires a still field which means that the heart must be stopped. In order to accomplish this, the patient must be placed on a machine which pumps and oxygenates the blood (pump-oxygenator or heat-lung pump). Upon completion of the CABG, the heart must then be restarted. Since coronary blood flow is cut off during the procedure, the heart may undergo varying degrees of ischemia which may impair the ability of the heart to resume normal function. Thromboxane A₂ (TXA) antagonists have been found to improve this return of function in various models of short-term myocardial ischemia simulating CABG, Grover, G. J., et al., "Thromboxane A₂ Antagonist and Diltiazem Induced Enhancement of Contractile Function: The Effect of Timing of Treatment" (Submitted for publication). One other serious problem encountered during this procedure is the severe platelet loss due to the heart-lung pump, McKenna, R. F., et al., "The Hemostatic Mechanism after Open-heart surgery", J. Thorac. Cardiovasc. Surg. 70: 298, 1975. Thus, to reduce post-surgical bleeding, these patients must be transfused with platelet rich blood with its concomitant risk of infections.

It would thus be an advance in the art to find a means of reducing this platelet loss without an untoward effect on the CABG procedure itself. Although the nature of the platelet loss is not fully understood, it is believed that it is due to contact with the synthetic surfaces of the extracorporeal perfusion circuit. This interaction is associated with the release of TXA which is a powerful platelet aggregating agent, Ogletree, M. L., "Overview of Physiological and Pathophysiological Effects of Thromboxane A₂", Fed. Proc. 46: 133, 1987. While aspirin has been found to be ineffective in inhibiting platelet loss in models of CABG, Addonizio, V. P., et al., "Thromboxane Synthesis and Platelet Secretion during Cardiopulmonary Bypass with Bubble Oxygenator", J. Thorac. Cardiovasc. Surg. 79: 91, 1980, prostacyclin significantly reduces platelet loss in similar models, Wonder, T., et al., "Preservation of Platelet Number and Function During Extracorporeal Membrane Oxygenation (ECMO) by Regional Infusion of PGI₂", Circulation 58: II-207, 1978. The problem with administration of prostacyclin to the patient is that it results in a severe and dose-dependent systemic hypotension. Thus, a compound which could reduce platelet loss by itself without untoward hemodynamic consequences or combined with prostacyclin in such a manner as to minimize its hypotensive effects would be important in improving the CABG procedure and other procedures that involve extracorporeal circulation of the blood.

DESCRIPTION OF THE INVENTION

In accordance with the present invention, a method is provided for preventing or reducing platelet loss during extracorporeal circulation such as during coronary artery bypass and graft procedures where a heart-lung pump or pump-oxygenator is employed or during kidney dialysis, in mammalian species, wherein a therapeutically effective amount of a thromboxane A₂ receptor antagonist is systemically administered, such as orally or parenterally, alone or in conjunction with prostacyclin and/or a prostacyclin mimic.

The thromboxane A₂ antagonist will prevent or reduce platelet loss without causing a reduction in blood pressure. Therefore, the thromboxane A₂ antagonist when used alone would be more attractive than prostacyclin for single drug treatment.

As indicated, the thromboxane antagonist may be employed in conjunction or combination with prostacyclin and/or a prostacyclin mimic wherein reduced amounts of prostacyclin or prostacyclin mimic will be included to reduce hypotensive side effects thereof. Thus, the thromboxane antagonist will be employed in a weight ratio to prostacyclin of within the range of from about 2:1 to about 2000:1, and preferably from about 10:1 to about 500:1.

Thromboxane A₂ receptor antagonists which may be employed herein include the 7-oxabicycloheptane and 7-oxabicycloheptene compounds disclosed in U.S. Pat. No. 4,537,981 to Snitman et al, especially, [1S-[1α,2β(5Z),3β(1E,3R,4S),4α]]-7-[3-(3-hydroxy-4-phenyl-1-pentenyl)-7-oxabicyclo-[2.2.1]hept-2-yl]-5-heptenoic acid; the 7-oxabicycloheptane substituted aminoprostaglandin analogs disclosed in U.S. Pat. No. 4,416,896 to Nakane et al., especially, [1S-[1α,2β(5Z),3β,4α]]-7-[3-[[2-(phenylamino)carbonyl]hydrazino]methyl]-7-oxabicyclo[2.2.1]hept-2-yl]-5-heptenoic acid; the 7-oxabicycloheptane substituted diamide prostaglandin analogs disclosed in U.S. Pat. No. 4,663,336 to Nakane et al, especially, [1S-[1β,2α(5Z),3α,4β]]-7-[3-[[[[(1-oxoheptyl)-amino]acetyl]amino]methyl]-7-oxabicyclo[2.2.1]-hept-2-yl]-5-heptenoic acid and the corresponding tetrazole, and [1S-[1<α,2<β(Z),3<β,4<α]]-7-[3-[[[[(4-cyclohexyl-1-oxobutyl)amino]acetyl]amino]methyl]-7-oxabicyclo[2.2.1]hept-2-yl]-5-heptenoic acid; the phenoxyalkyl carboxylic acids disclosed in U.S. Pat. No. 4,258,058 to Witte et al, especially 4-[2-(benzenesulfamido)ethyl]phenoxyacetic acid, (BM 13,177—Boehringer Mannheim), the sulphonamidophenyl carboxylic acids disclosed in U.S. Pat. No. 4,443,477 to Witte et al, especially 4-[2-(4-chlorobenzenesulfonamido)-ethyl]phenylacetic acid, (BM 13,505, Boehringer Mannheim) the arylthioalkylphenyl carboxylic acids disclosed in U.S. application Ser. No. 067,199 filed June 29, 1987, especially 4-(3-((4-chlorophenyl)sulfonyl)propyl)benzeneacetic acid.

Other examples of thromboxane A₂ receptor antagonists suitable for use herein include, but are not limited to (E)-5-[[[(pyridinyl)[3-(trifluoromethyl)phenyl]methylene]amino]oxy]pentanoic acid also referred to as R68,070—Janssen Research Laboratories, 3-[1-(4-chlorophenylmethyl)-5-fluoro-3-methylindol-2-yl]-2,2- dimethylpropanoic acid [(L-655240 Merck-Frosst) Eur. J. Pharmacol. 135(2): 193, 17 March 87], 5(Z)-7-([2,4,5-cis]-4-(2-hydroxyphenyl)-2-trifluoromethyl-1,3-dioxan-5-yl)heptenoic acid (ICI 185282, Brit. J. Pharmacol 90 (Proc. Suppl): 228 P-Abs., March 87), 5(Z)-7-[2,2-dimethyl-4-phenyl-1,3-dioxan-cis-5-yl]heptenoic acid (ICI 159995, Brit. J. Pharmacol. 86 (Proc. Suppl): 808 P-Abs., December 85), N,N'-bis[7-(3-chlorobenzeneaminosulfonyl)-1,2,3,4-tetrahydro-isoquinolyl]-disulfonylimide (SKF 88046, Pharmacologist 25(3): 116 Abs, 117 Abs, August 83), [1α(Z)-2β,5α]-(+)-7-[5-[[(1,1'-biphenyl)-4-yl]-methoxy]-2-(4-morpholinyl)-3-oxocyclopentyl]-4-heptenoic acid (AH 23848—Glaxo, Circulation 72(6): 1208, December 85, levallorphan allyl bromide (CM 32,191, Sanofi, Life Sci. 31 (20–21): 2261, 15 November 82), (Z,2-endo-3-oxo)-7-(3-acetyl-2-bicyclo[2.2.1]heptyl-5-hepta-3Z-enoic acid, 4-phenyl-thiosemicarbazone (EP092—Univ. Edinburgh, Brit, J. Pharmacol. 84(3): 595, March 85).

Prostacyclin mimics which may be employed with the thromboxane $A_2$ antagonist include, but are not limited to, Cicaprost (Schering AG)

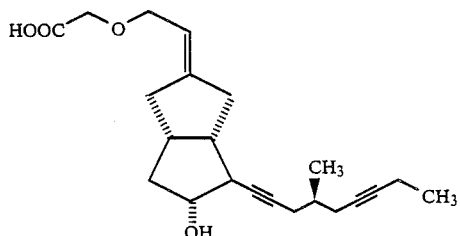

CG-4203 (Grunenthal)

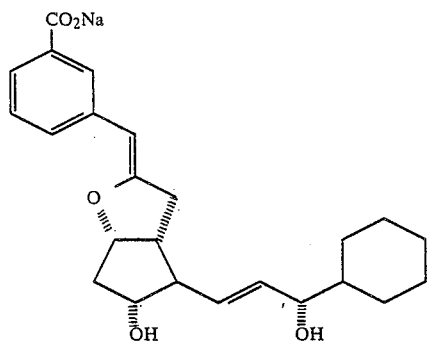

FCE-22509 (Erbamont)

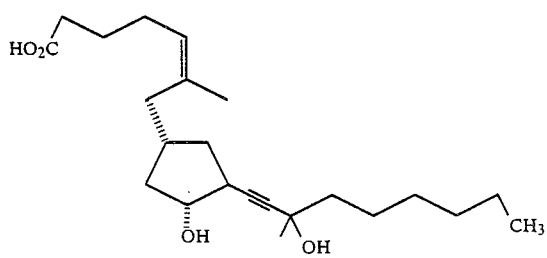

FCE-21292

+

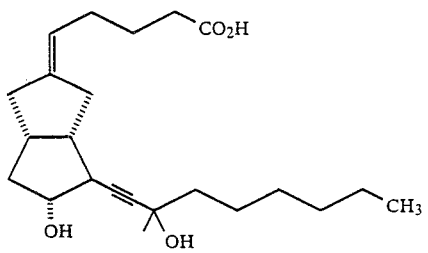

FCE-21291

Iloprost (Schering AG; Eisai)

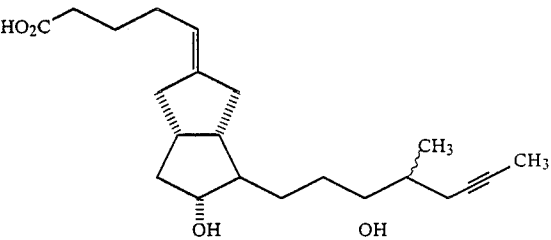

OP-41483 (Ono; Dainippon)

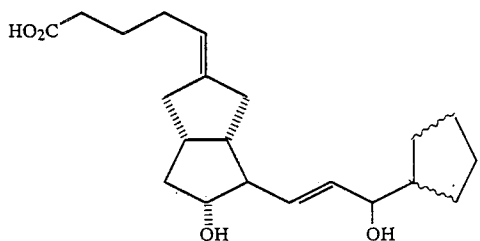

TRK-100 (Toray)

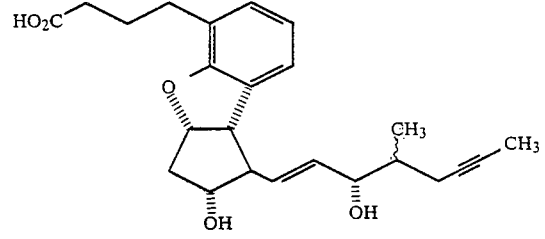

The disclosure of the above-mentioned patents, patent applications and other references are incorporated herein by reference.

In carrying out the method of the present invention, the thromboxane $A_2$ antagonist alone or with prostacyclin and/or the prostacyclin mimic may be administered to mammalian species, such as monkeys, dogs, cats, rats, humans, etc. within from about 1 to about 2 hours of and/or during the period of extracorporeal circulation and/or shortly after termination of extracorporeal circulation, for example within from about 1 to about 2 hours after surgery.

The thromboxane $A_2$ antagonist alone or with prostacyclin and/or prostacyclin mimic may be administered systemically, such as orally (prior to extracorporeal circulation) or parenterally, as well as locally to the coronary arteries by catheter such as by arterial angiography or intracoronary injection.

With regard to dosage of thromboxane $A_2$ antagonist, where the drug is administered by catheter (arterial angiography) or intracoronary injection, from about 0.1 to about 30 mg/kg/treatment and preferably from about 0.5 to about 25 mg/kg/treatment will be employed. The number of treatments will depend upon the length of the extracorporeal circulation platelet loss encountered during such period. Usually, from 1 to 5 treatments per day will be required.

Where prostacyclin and/or prostacyclin mimic are administered by cathether or intracoronary injection, from about 0.0008 to about 0.225 mg/kg/treatment and preferably from about 0.004 to about 0.19 mg/kg treatment will be employed.

Where the thromboxane $A_2$ antagonist alone or in combination with prostacyclin and/or prostacyclin mimic is to be administered by angiography or intracoronary injection, it (or the combination) will be formulated in a conventional vehicle, such as distilled water, saline, Ringer's solution, or other conventional carriers.

The thromboxane $A_2$ alone or in combination with prostacyclin and/or prostacyclin mimic may also be incorporated in a conventional dosage form, such as a tablet, capsule or elixir (to be used prior to extracorporeal circulation) or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

The thromboxane $A_2$ antagonist may be employed in a separate dosge form from the prostacyclin and/or prostacyclin mimic such as two separate injections or the two may be employed in a single dosage form, such as a single injection.

With regard to such systemic formulations, where the thromboxane $A_2$ antagonist is to be employed alone, single or divided doses of from about 5 to about 2500 mg, preferably from about 10 to about 2000 mg/one to four times daily, may be administered in systemic dosage forms as described above.

With regard to combinations of the thromboxane $A_2$ antagonist with prostacyclin and/or prostacyclin mimic, single or divided doses of from 2 to about 2000 mg of thromboxane $A_2$ antagonist, preferably 5 to 1500 mg thromboxane $A_2$ antagonist, and from about 0.015 to about 15 mg prostacyclin and/or prostacyclin mimic and preferably from about 0.037 to about 11.25 mg prostacyclin and/or prostacyclin mimic may be administered one to four times daily.

The thromboxane $A_2$ antagonist alone or with the prostacyclin and/or prostacyclin mimic may be administered prior to and throughout the period of extracorporeal circulation and subsequently thereto.

REFERENCE TO ACCOMPANYING FIGURE

The accompanying FIGURE is a graph of the effect of intravenous thromboxane $A_2$ antagonist (SQ 30,741) on platelet reduction during bypass surgery.

The following Examples represent preferred embodiments of the present invention.

EXAMPLE 1

An injectable solution of thromboxane $A_2$ receptor antagonist for intravenous use in preventing or reducing platelet loss during extracorporeal circulation is produced as follows:

| | |
|---|---|
| [1S—[1α, 2β(5Z), 3β, 4α]]-7-[3-[[2-(phenylamino)carbonyl]hydrazino]-methyl]-7-oxabicyclo[2.2.1]hept-2-yl]-5-heptenoic acid (SQ 29,548) | 2500 mg |
| Methyl paraben | 5 mg |
| Propyl paraben | 1 mg |
| Sodium chloride | 25 g |
| Water for injection qs. | 5 l. |

The thromboxane $A_2$ receptor antagonist, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains a concentration of 75 mg of active ingredient per 150 ml of solution.

EXAMPLE 2

An injectable for use in treating or preventing platelet loss during extracorporeal circulation is prepared as described in Example 1 except that the thromboxane $A_2$ receptor antagonist employed is the phenoxyalkyl carboxylic acid 4-[2-(benzenesulfamido)ethyl]phenoxyacetic acid, disclosed in U.S. Pat. No. 4,258,058.

EXAMPLE 3

An injectable solution of thromboxane $A_2$ receptor antagonist for intravenous use containing [1S-[1β,2α(5Z),3α,4β]]-7-[3-[[[[(1-oxoheptyl)amino]acetyl]amino]methyl]-7-oxabicyclo[2.2.1]hept-2-yl]-5-heptenoic acid (SQ 30,741) as the thromboxane $A_2$ receptor antagonist is prepared as described in Example 1 except that 11 mg of prostacyclin are included.

EXAMPLE 4

An injectable for use in preventing or reducing platelet loss is prepared as described in Example 1 except that the thromboxane $A_2$ receptor antagonist employed is [1S-[1<α,2<β(Z),3<β,4<α]]-7-[3-[[[[(4-cyclohexyl-1-oxobutyl)amino]acetyl]amino]methyl]-7-oxabicyclo[2.2.1]hept-2-yl]-5-heptenoic acid and 11 mg of prostacyclin are included.

EXAMPLE 5

A thromboxane $A_2$ antagonist formulation suitable for oral administration is set out below.

1000 tablets each containing 400 mg of thromboxane $A_2$ receptor antagonist were produced from the following ingredients.

| | |
|---|---|
| [1S—[1β, 2α(5Z), 3α, 4β]]-7-[3-[[[[(1-Oxoheptyl)amino]acetyl]amino]methyl]-7-oxabicyclo[2.2.1]hept-2-yl]-5-heptenoic acid (SQ 30,741) | 400 g |
| Corn starch | 50 g |
| Gelatin | 7.5 g |
| Avicel (microcrystalline cellulose) | 25 g |
| Magnesium stearate | 2.5 g |

The thromboxane $A_2$ receptor antagonist and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 400 mg of active ingredient.

EXAMPLE 6

An injectable for use in preventing or reducing platelet loss is prepared as described in Example 3 except that a prostacyclin mimic is included in place of prostacyclin, which prostacyclin mimic may be CG-4203 (Grünenthal), FCE-22509 (Erbamont), Iloprost (Schering AG; Eisai), OP-41483 (Ono; Dainippon), Cicaprost (Schering AG), or TRK-100 (Toray).

EXAMPLE 7

The following Experiment was conducted to determine the effect of the thromboxane $A_2$ antagonist SQ 30,741 on platelet loss during coronary bypass surgery.

Adult anesthetized dogs were intubated and placed on artificial respiration. A left thoracotomy was performed at the fifth intercostal space and the pericardium was resected. Hemodynamic and blood gas parameters were measured before the animals were placed on cardiopulmonary bypass. Baseline platelet counts were also taken immediately before bypass. At this time, the animals were treated with intravenous saline (n=6) or SQ 30,741 at a dose of 5 mg/kg+5 mg/kg/min (n=7) 10 minutes before bypass. The animals were then placed on total, vented cardiopulmonary bypass as previously described by J. Vinten-Johansen, "Superiority of Surgical Versus Medical Reperfusion After Regional Ischemia," *J. Thorac. Cardiovasc. Surg.* 92: 525, 1986. The animals were maintained on bypass for a total of 30 minutes. The bypass was performed under normothermic conditions without cardioplegia. Platelet counts were performed at 1, 3, 5, 10 and 30 minutes into the bypass.

RESULTS

Platelet count in the blood is expressed as a percent of baseline values on the accompanying FIGURE. There was a rapid loss of platelets upon institution of the bypass in both drug and saline treated animals. However, platelet loss was significantly diminished in animals treated with SQ 30,741. These data indicate that thromboxane receptor blockade via SQ 30,741 can act to reduce platelet loss. This platelet preservation seems to be occurring at a dose which is also resulting in myocardial protection during bypass making this compound doubly useful during CABG procedures.

What is claimed is:

1. A method for preventing or reducing platelet loss during extracorporeal circulation, in a mammalian species, which comprises administering to a mammalian species in need of such treatment an effective amount of a thromboxane $A_2$ receptor antagonist alone or with an effective amount of prostacyclin and/or a prostacyclin mimic, said thromboxane $A_2$ receptor antagonist being a 7-oxabicycloheptane or a 7-oxabicycloheptane derivative.

2. The method as defined in claim 1 wherein the thromboxane $A_2$ antagonist is administered alone.

3. The method as defined in claim 1 wherein the thromboxane $A_2$ antagonist is administered with prostacyclin and/or a prostacyclin mimic.

4. The method as defined in claim 1 wherein the thromboxane $A_2$ antagonist is employed in a weight ratio to prostacyclin and/or a prostacyclin mimic of within the range of from about 2:1 to about 2000:1.

5. The method as defined in claim 1 wherein the thromboxane $A_2$ receptor antagonist alone or with prostacyclin and/or a prostacyclin mimic is administered systemically.

6. The method as defined in claim 1 wherein the thromboxane $A_2$ receptor antagonist alone or with prostacyclin and/or a prostacyclin mimic is administered intravenously.

7. The method as defined in claim 1 wherein the thromboxane $A_2$ receptor antagonist alone or with prostacyclin and/or a prostacyclin mimic is administered during extracorporeal circulation.

8. The method as defined in claim 1 wherein the thromboxane $A_2$ receptor antagonist alone or with prostacyclin and/or a prostacyclin mimic is administered prior to extracorporeal circulation.

9. The method as defined in claim 1 wherein the thromboxane $A_2$ receptor antagonist when used with prostacyclin or a prostacyclin mimic is a 7-oxabicycloheptane.

10. The method as defined in claim 1 wherein the thromboxane $A_2$ receptor antagonist is a 7-oxabicycloheptane substituted amino-prostaglandin analog.

11. The method as defined in claim 1 wherein the thromboxane $A_2$ receptor antagonist is a 7-oxabicycloheptane substituted diamide prostaglandin analog.

12. The method as defined in claim 1 wherein the thromboxane $A_2$ receptor antagonist is a phenoxyalkyl carboxylic acid.

13. The method as defined in claim 1 wherein the thromboxane $A_2$ receptor antagonist is a sulfonamidophenyl carboxylic acid.

14. The method as defined in claim 1 wherein the thromoboxane $A_2$ receptor antagonist is an arylthioalkylphenyl carboxylic acid.

15. The method as defined in claim 1 wherein the thromboxane $A_2$ receptor antagonist is [1S-[1α,2β(5Z),3β(1E,3R,4S),4α]]-7-[3-(3-hydroxy-4-phenyl-1-pentenyl)-7-oxabicyclo[2.2.1]hept-2-yl]-5-heptenoic acid.

16. The method as defined in claim 1 wherein the thromboxane $A_2$ receptor antagonist has the name [1S-[1β,2α(5Z),3α,4β]]-7-[3-[[[[(1-oxoheptyl)amino]acetyl]amino]methyl]-7-oxabicyclo[2.2.1]hept-2-yl]-5-heptenoic acid or the corresponding tetrazole.

17. The method as defined in claim 1 wherein the thromboxane $A_2$ receptor antagonist has the name [1S-[1<α,2<β(Z),3<β,4<α]]-7-[3-[[[[(4-cyclohexyl-1-oxobutyl)amino]acetyl]amino]methyl]-7-oxabicyclo[2.2.1]hept-2-yl]-5-heptanoic acid.

18. The method as defined in claim 1 wherein the thromboxane $A_2$ receptor antagonist has the name [1S-[1α,2β(5Z),3β,4α]]-7-[3-[[2-(phenylamino)carbonyl]hydrazino]methyl]-7-oxabicyclo[2.2.1]hept-2-yl]-5-heptenoic acid.

19. The method as defined in claim 1 wherein the thromboxane $A_2$ receptor antagonist has the name 4-(3-((4-chlorophenyl)sulfonyl)propyl)benzene acetic acid.

20. The method as defined in claim 1 wherein the thromboxane $A_2$ receptor antagonist has the name or 4-[2-(benzenesulfamido)ethyl]phenoxyacetic acid or 4-[2-(4-chlorobenzenesulfonamido)ethyl]phenylacetic acid.

* * * * *